Figure 1:
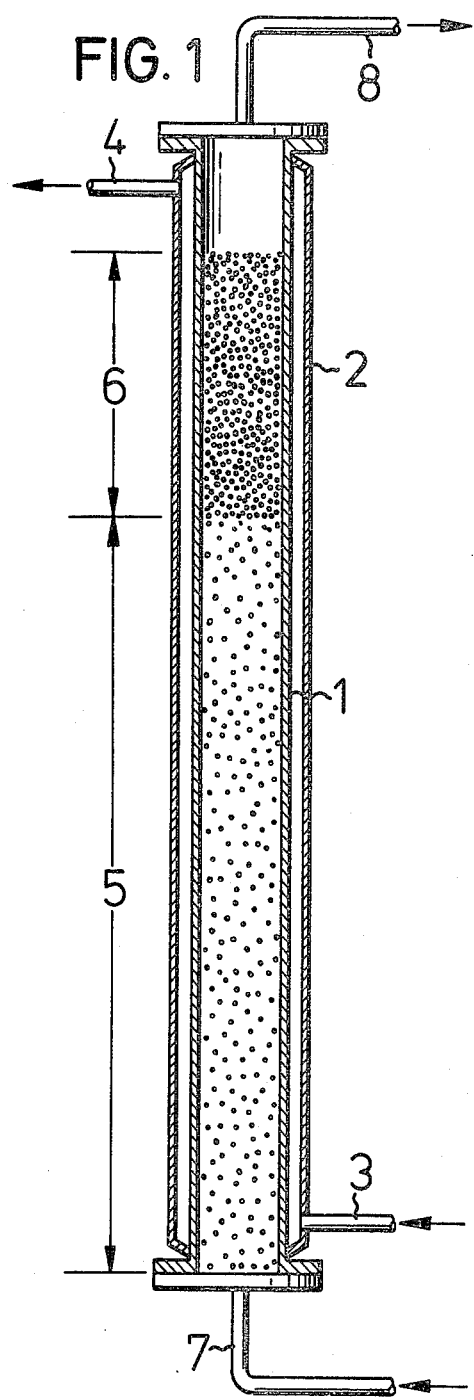

United States Patent [19]

Rebsdat et al.

[11] 4,177,169

[45] Dec. 4, 1979

[54] PROCESS FOR IMPROVING THE ACTIVITY OF USED SUPPORTED SILVER CATALYSTS

[75] Inventors: Siegfried Rebsdat, Burg; Sigmund Mayer, Burgkirchen; Josef Alfranseder, Marktl; Josef Riedl, Burgkirchen, all of Fed. Rep. of Germany

[73] Assignee: Hoechst Aktiengesellschaft, Fed. Rep. of Germany

[21] Appl. No.: 845,563

[22] Filed: Oct. 26, 1977

[30] Foreign Application Priority Data

Oct. 29, 1976 [DE] Fed. Rep. of Germany ....... 2649359

[51] Int. Cl.² .................. B01J 23/50; B01J 23/96; C07D 301/10; C07D 303/04
[52] U.S. Cl. .................................. 252/476; 252/412; 252/414; 260/348.34
[58] Field of Search ............... 252/411, 412, 414, 476; 260/348.34

[56] References Cited

U.S. PATENT DOCUMENTS

| 4,033,903 | 7/1977 | Maxwell | 252/476 |
| 4,051,068 | 9/1977 | Rebsdat et al. | 252/412 |

Primary Examiner—P. E. Konopka
Attorney, Agent, or Firm—Connolly and Hutz

[57] ABSTRACT

The activity of supported silver catalysts for the direct oxidation of ethylene to ethylene oxide with molecular oxygen or air is improved by applying to the catalyst from 1 to 1,000 ppm, preferably 20 to 500 ppm, of cesium and/or rubidium in two or more than two steps and using the catalyst after each impregnation step again for the production of ethylene oxide by direct oxidation of ethylene with molecular oxygen or air.

2 Claims, 2 Drawing Figures

○ one-step Cs impregnation catalyst type I
× one-step Cs impregnation catalyst type II
□ two-step Cs impregnation catalyst type I
■ two-step Cs impregnation catalyst type II
△ three-step Cs impregnation catalyst type I
▲ three-step Cs impregnation catalyst type II

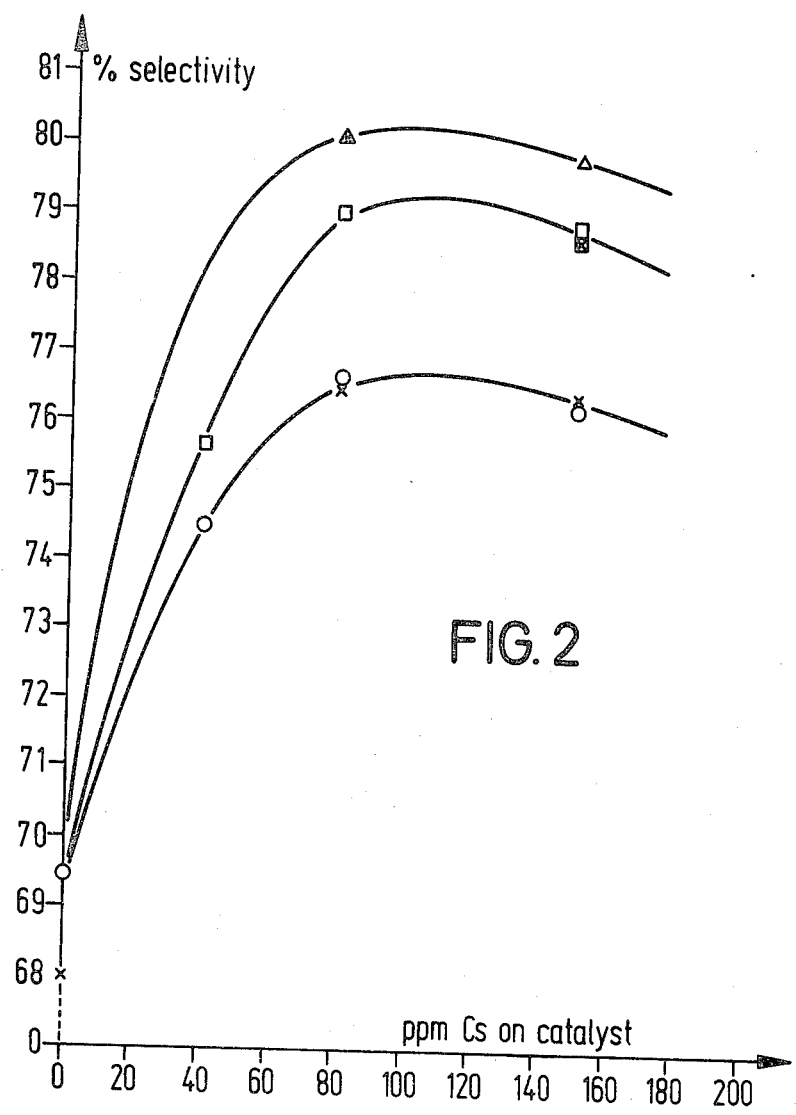

PROCESS FOR IMPROVING THE ACTIVITY OF USED SUPPORTED SILVER CATALYSTS

This invention relates to a process for improving the activity of supported silver catalysts for the direct oxidation of ethylene to ethylene oxide with molecular oxygen or air, by applying to the catalyst, which has already been used in the direct oxidation, from 1 to 1,000 parts of caesium and/or rubidium per 1 million parts of catalyst with the aid of an impregnating liquid containing caesium and/or rubidium compounds, which comprises impregnating the catalyst in two or more steps and, after each individual impregnation, using the catalyst again for the direct oxidation of ethylene with molecular oxygen or air.

For the manufacture of ethylene oxide by oxidation of ethylene with oxygen or air silver catalysts are used the preparation of which is known for a long time and described in various patent specifications. A substantial number of large-scale industrial installations for the manufacture of ethylene oxide operate in accordance with the silver catalyst process. In this process, usually only a fraction of the ethylene employed is reacted. The predominant portion of the reacted ethylene is converted into ethylene oxide with oxygen on the carrier material impregnated with silver, while the remainder is virtually completely converted into carbon dioxide and water.

In the course of time, the most diverse silver catalysts have been developed and in particular with the aim of increasing the selectivity with respect to the preferred formation of ethylene oxide and of suppressing the formation of $CO_2$ and water.

With rising prices of raw materials and increasing scarcity of raw materials, an increased selectivity of the catalyst is of particular economic importance. Thus, in recent years silver catalysts, the selectivity of which for ethylene oxide is up to 75% compared with earlier types with a selectivity of only 65 to 70%, have been successfully developed. These catalysts, such as described, for example, in German Offenlegungsschrift No. 2,300,512, are obtained by applying to an inert support material, such as, for example, $Al_2O_3$, at the same time as the silver, 0.0004 to 0.0027 g equivalent of a potassium, rubidium or caesium compound per kg of catalyst from an aqueous solution. On the other hand, it is also known that silver catalysts lose their selectivity in the course of time, and after being used for a number of years must be replaced by new catalyst. Apart from the costs of materials, the exchange of an "exhausted" catalyst for a new one in large-scale industrial installations is extremely time-consuming and labor-intensive; in addition, it causes loss in production and high costs. Accordingly, there is the problem of whether it is possible to improve the selectivity of exhausted catalysts again by a simple treatment in order to avoid or put off for as long as possible the exchange for a new catalyst.

Such a process is described in German Auslegeschrift No. 2,519,599. In this process, a silver catalyst which has already been in use for a relatively long time is impregnated with a caesium nitrate and/or rubidium nitrate solution in an aliphatic alcohol containing water, on the catalyst a concentration of from 1 to 1,000 ppm by weight of caesium and/or rubidium is adjusted and, after allowing the solution to run off, the alcohol remaining on the catalyst is evaporated at 70° to 120° C., whilst simultaneously passing nitrogen through. The selectivity of the catalyst treated in this manner is improved considerably.

The present invention provides a process for improving the activity of used silver catalysts which is superior to the process described in German Auslegeschrift No. 2,519,599.

It has been found that the activity of a supported silver catalyst, which has already been used in the direct oxidation of ethylene with molecular oxygen or air and which, after the treatment with an impregnation solution containing caesium and/or rubidium compounds, contains from 1 to 1,000 parts by weight of caesium and/or rubidium per one million parts by weight of catalyst, can be improved by applying the caesium and/or rubidium in two or more steps and using the catalyst after each treatment again for the production of ethylene oxide. The time during which the catalyst to be treated was in use for the oxidation of ethylene to ethylene oxide prior to the treatment according to the invention can vary between a few weeks and several years. It is not absolutely necessary that the activity of the catalyst has subsided, i.e. its selectivity is reduced. The effect of the treatment is the better the greater the loss of the original selectivity of the catalyst.

The impregnating liquid should contain the caesium compounds and/or rubidium compounds in a form which is as finely divided as possible. The compounds mentioned can be present in dispersion or emulsion, but they are preferably used in the dissolved form.

Organic substances which are inert towards the catalyst are used as the solvent or liquid phase of a dispersion, and preferably those which have an average good volatility. For example, one or more compounds, with up to about 10 carbon atoms, of the following nature can be used: linear, branched or cyclic, optionally aromatic hydrocarbons; ketones; carboxylic acid esters or amides or dicarboxylic acid esters or amides; primary, secondary or tertiary amines or ethers. Aliphatic linear, branched or cyclic alcohols with up to about 10 carbon atoms, preferably with 1 to 8 carbon atoms, are preferably used and in particular those with up to 3 carbon atoms, such as ethanol, propanol and isopropanol, methanol being particularly preferred. Mixtures of the aforesaid liquids can also be used.

Up to 40% by weight, relative to the total liquid, of water can optionally be added to these organic substances, for example in order to facilitate solution of the caesium and/or rubidium compounds. However, in general purely aqueous solutions of the compounds mentioned should not be used since they have an unfavorable influence on the activity of the catalyst. This decrease of activity by purely aqueous solution is, however, reversible, i.e. it may be compensated by special activating reaction conditions, for example increased temperature, whereby the activity is improved as intended by the treatment of the invention. The use of purely aqueous impregnating liquids is thus possible, on principle, but for practical considerations it is not expedient.

Virtually, only the amount of caesium and/or rubidium applied to the catalyst, in general in the form of the corresponding cations, is decisive for the effect according to the invention. It is of little importance with which radical (anion) caesium and/or rubidium is associated. The radicals can be inorganic or organic but they should not consist of substances which, in particular after the treatment with the gaseous reaction mixture for the production of ethylene oxide at 230° to 270° C., act as so-called "catalyst poison." Preferably, inorganic or organic salts, hydroxides, alcoholates or phenolates of caesium and rubidium are used. Particularly preferred are the salts, especially inorganic salts, hydroxides and alcoholates. Suitable radicals (anions) for the process of the invention are, for example, sulfate, nitrite, chloride, bromide, fluoride, chlorate, bromate, cyanate, silicate, oxalate, malonate, succinate, butyrate, laurate, stearate, benzoate, phenolate, and more preferably the formates, acetates, carbonates, bicarbonates, nitrates, hydroxides, or alcoholates of aliphatic alcohols having from 1 to 3 carbon atoms.

Either one or more caesium or rubidium compounds can be used and mixtures of caesium compounds and rubidium compounds are also suitable. The concentration of the caesium compound and/or rubidium compound in the impregnating liquid can be varied within wide limits, it is preferably chosen so that 0.003 to 0.6% by weight of caesium and/or rubidium is present, relative to the total impregnating liquid.

The content of caesium and/or rubidium in the supported silver catalyst after the treatment according to the invention should be 1 to 1,000 ppm. If the content of caesium and/or rubidium is below 1 or above 1,000 ppm, a significant improvement in the selectivity by the process of the invention can no longer be detected.

To apply the caesium and/or rubidium to the catalyst it is suitably treated (wetted) with the impregnating liquid, for example by spraying the liquid onto the catalyst or by pouring it thereover. It proved most convenient and simple to place the catalyst to be treated in a container and to pour the impregnating liquid thereover to a level a little over the level of the catalyst particles.

The impregnating liquid should be used in an amount such that the catalyst particles are completely wetted. There is no upper limit for the amount of impregnating liquid with respect to the effect. Considering the expenditure and the effect, to obtain a favorable result the impregnating liquid is generally used in an amount of from 75 to 150%, calculated on the catalyst to be treated. The time of action of the impregnating liquid on the catalyst is not critical. In general, the impregnating liquid will be allowed to flow off after a time of action of about 3 to 120 minutes, preferably 5 to 20 minutes and drained from the catalyst particles.

After draining, the volatile constituents of the impregnating liquid are removed by heating, optionally while simultaneously passing over an inert gas. Suitable inert gases are non-flammable gases which do not promote combustion, such as nitrogen or carbon dioxide. As long as sources of ignition are eliminated and/or a large excess of the gas is used, which does not form flammable mixtures with the volatile substances, other gases, in particular air, can also be used.

After applying to the used catalyst, in the first treatment step, at least 1 ppm of caesium and/or rubidium, preferably 10 to 300 ppm, by the treatment with the impregnating liquid, the catalyst is used again for the direct oxidation of ethylene to ethylene oxide with molecular oxygen or air. The time of use of the treated catalyst can vary within wide limits, in general it is at least one day, preferably 2 to 60 weeks and more preferably 2 to 20 weeks. There is no upper limit for the time of use. After the use of the catalyst, it is treated a second time with the impregnating liquid according to the invention. The applied amount of caesium and/or rubidium in the second treatment can be varied within wide limits, it is preferably in the range of from 5 to 100 ppm. After the second treatment with the impregnating liquid, the catalyst is used again for the production.

According to the invention, the used catalyst should be treated with the impregnating liquid at least two times. However, the number of treatments with the impregnating liquid can be as high as desired and, after each individual treatment, the catalyst is used again for the production of ethylene oxide by direct oxidation of ethylene with oxygen or air. The number of treatments is mainly dependent on practical considerations. It proved advantageous to treat the catalyst 2 to 8 times, preferably 2 to 4 times with the impregnating liquid. The amount of caesium and/or rubidium applied in each treatment step depends on the total amount to be applied, which is preferably in the range of from 20 to 500 ppm of caesium and/or rubidium after having applied in the first treatment at least 1 ppm, preferably 10 to 300 ppm of caesium and/or rubidium. In general, in the following treatments with the impregnating liquid in each step at least 5 and preferably 5 to 100 ppm of caesium and/or rubidium are applied. The periods of time for which the catalyst is used again after the first, second, third, fourth and possibly further treatment steps can be identical or different within the aforesaid limits.

According to the invention a more important increase in the activity of used catalysts is obtained by applying a specific caesium and/or rubidium content not all at once, as proposed in German Auslegeschrift No. 2,519,599, but in several steps and by using the catalyst between the individual steps of treatment for the production of ethylene oxide, preferably for a period of at least 2 weeks.

The following examples illustrate the invention and demonstrate the surprisingly high increase in the activity.

The test reactor shown in FIG. 1 of the accompanying drawing consisted of a reaction tube 1 made of chrome-vanadium steel and having an internal diameter of 30 mm and a length of 300 mm. The reaction tube 1 was provided with a jacket 2 through which heated oil, entering at 3 and issuing at 4, was circulated. Zone 5 of the reaction tube 1 (length 200 mm) contained $\alpha$-$Al_2O_3$ and was used to pre-heat the feed gas. Zone 6 (length 70 mm) of the reaction tube 1 contained the catalyst. The feed gas was introduced into reaction tube 1 through conduit 7 and it left the reactor through conduit 8.

The gas mixture used consisted of
28% of $C_2H_4$
53% of $CH_4$
8% of $O_2$
5% of $CO_2$
6% of $N_2$ and contained additionally 2 ppm of vinyl chloride as inhibitor.

The gas mixture leaving the reactor at the outlet was analyzed by gas chromatography and the conversion and the selectivity were calculated. The temperature of the heat carrier medium was varied until a constant ethylene conversion of 5% was reached. The tests were continued until the measured values remained constant, which was normally the case after a time of operation of 200 hours.

For the test, a supported silver catalyst was used which consisted of about 10.2% of silver on $\alpha Al_2O_3$ as carrier material. It had the shape of rings having a length of 8 mm, an external diameter of 8 mm and an internal diameter of 2 mm.

Two different types of the specified catalyst were used:

Type I: the described catalyst after an 8 week use in an industrial-scale ethylene oxide installation:
Type II: the described catalyst after a 2 year use in an industrial-scale ethylene oxide installation.

EXAMPLE 1

100 g of an impregnating solution prepared from
0.5 g of CsNO$_3$ tion, which were carried out in principle as described in Example 1. The conditions which are not in accordance with Example 1, namely caesium and rubidium content of the impregnating solution and of the catalyst, number of treatment steps, time of use between the treatment steps and the selectivity obtained are listed in the table.

The results are graphically evaluated in FIG. 2 of the accompanying drawing, in which the selectivity for a conversion of 5% is plotted as a function of the caesium content of the catalyst. It can be seen that with a stepwise application of caesium to the same final content, the selectivity is distinctly increased over an impregnation in one step.

| Example | Catalyst | Cs- and/or Rb-concentration in solution * ppm | Cs- and/or Rb-concentration on catalyst ppm | Selectivity % | temp. of heat carrier for 5% C$_2$H$_4$-conversion °C. | time of use between the treatment steps (weeks) |
|---|---|---|---|---|---|---|
| Comp. Ex. A | I | — | — | 69.5 | 245 | — |
| Comp. Ex. B | II | — | — | 68.0 | 247 | — |
| Comp. Ex. C | I | 900 | 150 | 76.2 | 241 | — |
| Ex. No. 1 | I | $^a$350 $^b$350 | 150 | 78.9 | 237 | 10 |
| Ex. No. 2 | I | $^a$350 $^b$180 $^c$100 | 150 | 79.9 | 231 | $a$–$b$ 11 $b$–$c$ 13 |
| Comp. Ex. D | I | 400 | 80 | 76.8 | 238 | |
| Ex. No. 3 | I | $^a$150 $^b$150 | 80 | 79.1 | 237 | 10 |
| Comp. Ex. E | I | 200 | 40 | 74.6 | 242 | |
| Ex. No. 4 | I | $^a$80 $^b$80 | 40 | 75.7 | 239 | 10 |
| Comp. Ex. F | II | 900 | 150 | 76.5 | 241 | |
| Ex. No. 5 | II | $^a$350 $^b$350 | 150 | 78.6 | 237 | 10 |
| Comp. Ex. G | II | 400 | 80 | 76.4 | 238 | |
| Ex. No. 6 | II | $^a$100 $^b$90 $^c$80 | 80 | 80.3 | 226 | $a$–$b$ 6 $b$–$c$ 15 |
| Comp. Ex. H | I | 400 | 80 (Rb) | 74.3 | 242 | |
| Ex. No. 7 | I | $^a$200 $^b$90 | 80 (Rb) | 75.6 | 240 | 10 |

* $a$, $b$, $c$ = individual steps of treatment 25.0 g of H$_2$O
974.5 g of CH$_3$OH were poured over 40 g of the aforesaid catalyst type I in a beaker. After 15 minutes the solution was decanted, the catalyst dried for 1 hours at 120° C. in a drying cabinet and then introduced into the test reactor. A gas current having the composition as specified above was passed over the catalyst at a space-time rate $$\frac{\text{parts by volume gas}}{\text{hours} \times \text{parts by volume catalyst}}$$

of 250 hour$^{-1}$ at atmospheric pressure. The temperature of the heating medium was adjusted so that the ethylene conversion amounted to 5%. After 200 hours, the heating medium had a temperature of 238° C. with an ethylene conversion of 5%.

The test was continued for 10 weeks. During this period of time no change in the measured values was observed. The test was then interrupted, the catalyst removed from the test reactor and treated again with the same impregnating solution as described above.

Thereafter, the catalyst was re-introduced into the reactor and the test was continued under the described conditions. The selectivity was found to be 76.5% with a temperature of the heating medium of 237° C.

In the following table are summarized the comparative examples and the examples according to the inven-

What is claimed is:

1. In a process for improving the selectivity of a supported silver catalyst for the direct oxidation of ethylene to ethylene oxide with molecular oxygen or air, of the type wherein on the used catalyst is applied caesuim, rubidium or mixture thereof by impregnating the used catalyst with an impregnating solution containing a compound of caesium, rubidium or mixture thereof, the improvement which comprises making said application at two different times interrupted by a period of using the catalyst, as follows:
   (a) making a first application on the catalyst of 10 to 300 ppm caesium, rubidium or mixture thereof;
   (b) thereafter using the catalyst for the production of ethylene oxide by direct oxidation of ethylene with molecular oxygen or air;
   (c) then interrupting said production after about 2 to 60 weeks, at the end of which time the selectivity of the catalyst is still at about the level which was achieved by said first application;
   (d) and next making a second application on the catalyst of 5 to 100 ppm caesium, rubidium or mixture thereof followed by using the resulting catalyst again for said production.

2. A process as claimed in claim 1, wherein the series of steps (a)–(d) is repeated about 2 to 8 times.

* * * * *